United States Patent [19]
Goodin et al.

[11] Patent Number: 5,421,405
[45] Date of Patent: Jun. 6, 1995

[54] HEAT EXCHANGER

[75] Inventors: Mark S. Goodin, Medina; Eric J. Thor, Columbia Heights, both of Minn.

[73] Assignee: Avecor Cardiovascular, Inc., Plymouth, Minn.

[21] Appl. No.: 163,893

[22] Filed: Dec. 7, 1993

[51] Int. Cl.$^6$ .................... F28D 7/10; A61M 1/14
[52] U.S. Cl. .................... 165/154; 165/164; 422/46
[58] Field of Search ............ 165/154, 164, 183, 165, 165/181, 178; 422/46

[56] References Cited

U.S. PATENT DOCUMENTS

| | | | |
|---|---|---|---|
| 1,649,097 | 11/1927 | Bryant | 165/154 |
| 2,050,281 | 8/1936 | Dietrich | 165/154 |
| 2,396,235 | 3/1946 | Arvins et al. | 165/141 |
| 2,620,167 | 12/1952 | Hopp | 165/154 |
| 2,723,880 | 11/1955 | Axelson | 239/139 |
| 3,326,280 | 6/1987 | Bosquain et al. | 165/161 |
| 3,468,631 | 9/1967 | Raible et al. | 422/46 |
| 3,731,731 | 5/1973 | Kyvsgaard et al. | 165/46 |
| 3,934,617 | 1/1976 | Henderson | 138/114 |
| 3,934,618 | 1/1976 | Henderson | 138/114 |
| 4,098,325 | 7/1978 | Scheel | 165/76 |
| 4,138,288 | 2/1979 | Lewin | 435/2 |
| 4,254,081 | 3/1981 | Streczyn et al. | 422/46 |
| 4,270,601 | 6/1981 | Lancaster | 165/154 |
| 4,280,981 | 7/1981 | Harnsberger | 422/46 |
| 4,374,088 | 2/1983 | Sternberg et al. | 422/46 |
| 4,437,513 | 3/1984 | Castiglioni et al. | 165/154 |
| 4,538,674 | 9/1985 | Schluderberg | 165/70 |
| 4,656,004 | 4/1987 | Stewart | 422/46 |
| 4,735,775 | 4/1988 | Leonard et al. | 422/46 |
| 4,902,476 | 2/1990 | Gordon et al. | 422/46 |
| 5,058,661 | 10/1991 | Oshiyama | 165/70 |
| 5,102,533 | 4/1992 | Oshiyama | 210/85 |
| 5,117,903 | 6/1992 | Oshiyama et al. | 165/158 |
| 5,120,501 | 6/1992 | Mathewson et al. | 422/46 |
| 5,152,964 | 10/1992 | Leonard | 422/48 |
| 5,209,906 | 5/1993 | Watkins et al. | 422/200 |
| 5,225,161 | 7/1993 | Mathewson et al. | 422/76 |

FOREIGN PATENT DOCUMENTS

| | | | |
|---|---|---|---|
| 719974 | 3/1942 | Germany | 165/154 |
| 107888 | 8/1980 | Japan | 165/154 |
| 201696 | 8/1923 | United Kingdom | 165/164 |
| 2146 | 2/1991 | WIPO | 165/164 |

*Primary Examiner*—John Rivell
*Assistant Examiner*—L. R. Leo
*Attorney, Agent, or Firm*—Popovich & Wiles

[57] ABSTRACT

A heat exchanger is provided for use in extracorporeal blood oxygenation systems. The heat exchanger includes a housing, a core disposed within the housing, and a baffle disposed within the core. A blood passage chamber is defined by the outer surface of the core and the inner surface of the housing. Blood flows from the blood inlet, through the blood passage chamber, to the blood outlet. Heat exchange fluids flow from a fluid inlet, into an inlet chamber, around the baffle, into an outlet chamber, and to a fluid outlet.

11 Claims, 6 Drawing Sheets

HEAT EXCHANGER

FIELD OF THE INVENTION

The present invention relates to an improved heat exchanger for use in the medical field. In particular, the present invention relates to a heat exchanger for use in extracorporeal blood oxygenation systems.

BACKGROUND OF THE INVENTION

Various surgical procedures, specifically cardiac surgical procedures, require an extracorporeal blood bypass circuit in order to bypass the area of the surgery. In cardiac surgical procedures, a complex extracorporeal blood circuit is created to bypass the heart while the surgery is performed. A typical extracorporeal blood circuit includes a venous and a cardiotomy blood reservoir, a mass transfer device (oxygenator) for effecting the carbon dioxide/oxygen exchange, a heat exchanger regulating the temperature of the blood before it is returned to the patient, and filters to remove any debris or gas bubbles entrained in the blood. The heat exchanger is formed integrally with the oxygenator or is closely associated therewith. It is desirable that the heat exchanger have high heat transfer efficiency and a low pressure drop.

Prior art heat exchangers use a corrugated metal core as the heat transfer barrier. The metal provides a good heat transfer characteristic and the corrugations increase surface area for heat transfer while minimizing the total size of the heat exchanger. Also, heat exchangers can be counter flow, i.e., a first fluid flows along the outside of the heat exchange barrier in one direction and a second fluid flows along the inside of the heat exchange barrier in the opposite direction.

In the case of a heat exchanger for use in an extracorporeal blood circuit, blood is being either warmed or cooled as it flows along one side of the heat exchange barrier and water, functioning as the heat exchange fluid, flows along the opposite side of the heat exchange barrier. The design criteria for the blood side of the heat exchanger are very different from the design criteria for the water side of the heat exchanger. On the blood side of the heat exchanger, the pressure drop from the input to the output of the heat exchanger must be minimized in order to use the heat exchanger within the complete extracorporeal blood circuit. Also, the blood side must be designed so that: (1) blood does not stagnate which can trap air bubbles and cause clotting; (2) blood is not subjected to shear forces which cause hemolysis or otherwise damage the blood; and (3) blood is not subjected to turbulence which can produce high shear forces and cause hemolysis or other blood damage.

The water side of the heat exchanger is not subjected to the limitations of operating within a complex biological circuit, therefore, concerns of pressure drop are limited to the pump performance characteristics of the heater/cooler. Also, water or other suitable heat exchange fluid is selected because it does not decompose or break down during use. The most important issue on the heat exchange fluid side is maximizing heat exchange efficiency.

One example of a prior art heat exchanger is disclosed in U.S. Pat. No. 4,635,755. In this device, a complex water manifold is disposed within a corrugated core, creating a narrow channel along the corrugations of the inner surface of the core. Water is confined to flowing circumferentially around the core in the convolutions.

Therefore, it is desirable to have a heat exchanger with a high heat transfer efficiency while having a simple, low-cost design.

SUMMARY OF THE INVENTION

In accordance with the present invention, a heat exchanger is provided for use in an extracorporeal blood circuit. The heat exchanger is constructed of a housing having opposed ends defining a longitudinal axis extending between the ends, and a continuous inner surface extending between the ends and along the longitudinal axis, forming an enclosed housing chamber.

A core is disposed within the housing chamber. The core has an inner surface and an outer surface extending between the ends along the longitudinal axis, wherein the ends, outer surface of the core and the inner surface of the housing define an enclosed annular blood passage chamber.

A baffle is disposed within the core and extending between the ends. The baffle has two opposed faces, two opposed edges, and an elongated cross section transverse to the longitudinal axis. Each edge is adjacent to the inner surface of the core. Each edge and adjacent inner surface defines an elongated portal along the longitudinal axis. One of the two opposed faces, the inner surface of the core and ends define an inlet chamber and the other of the two opposed faces, inner surface of the core and ends define an outlet chamber. The inlet chamber and outlet chamber are in fluid communication through the portals.

The heat exchanger is further constructed of a blood inlet in fluid communication with the blood passage chamber for introducing blood into the blood passage chamber and a blood outlet in fluid communication with the blood passage chamber for receiving blood from the blood passage chamber. A fluid inlet is in fluid communication with the inlet chamber and a fluid outlet is in fluid communication with the outlet chamber for passage of heat exchange fluid from the fluid inlet to the inlet chamber, through the portals into the outlet chamber, and out the fluid outlet.

It is preferred that the baffle be planar, having a substantially rectangular cross section transverse to the longitudinal axis and the core is corrugated and cylindrical relative to the longitudinal axis. The core optimally has approximately 15–18 corrugations per inch measured along the longitudinal axis. Each corrugation has a root defining the inner limit of the corrugation and a crest defining the outer limit of the corrugation and the distance from the root to the crest of each corrugation is less than one half inch.

It is further preferred that the fluid inlet has an inlet tube extending longitudinally from an end of the housing, said inlet tube having a plurality of apertures opening into the inlet chamber for introducing heat exchange fluid into the inlet chamber. The fluid outlet further has an outlet tube extending longitudinally from an end of the housing, said outlet tube having a plurality of apertures opening into the outlet chamber for receiving heat exchange fluid from the outlet chamber. The inlet and outlet tubes may extend from one end to the other end of the housing. The inlet and outlet tubes may also extend into the inlet and outlet chambers, respectively, and are spaced from the inner surface of the core and a face of the baffle. The respective apertures of the inlet and outlet tubes may be adjacent to the core and the apertures may be directed at the inner surface of the core. The respective apertures of the inlet and outlet tubes may have at least one row of apertures extending longitudinally along the tubes and the circumference of the apertures may decrease in size from one end to another.

In operation, blood is introduced into the blood passage chamber through the inlet and flows around the outer surface of the core and exits through the blood outlet. Water or other suitable heat exchange fluid is pumped into the fluid inlet at a high velocity and is directed into the inlet chamber. At the water flow rates normally used (10 to 20 liters/min) the flow is turbulent. The turbulent intensity is increased in the inlet chamber and vortices are created. Turbulent flow increases heat exchange efficiency in comparison to laminar flow. The turbulent water flows through the portals and into the outlet chamber. Water exits the outlet chamber through the fluid outlet.

DETAILED DESCRIPTION OF THE PREFERRED EMBODIMENT

The following detailed description and the accompanying drawings are provided for the purpose of describing embodiments of the invention and are not intended to limit the scope of the invention in any way.

Figure 1:
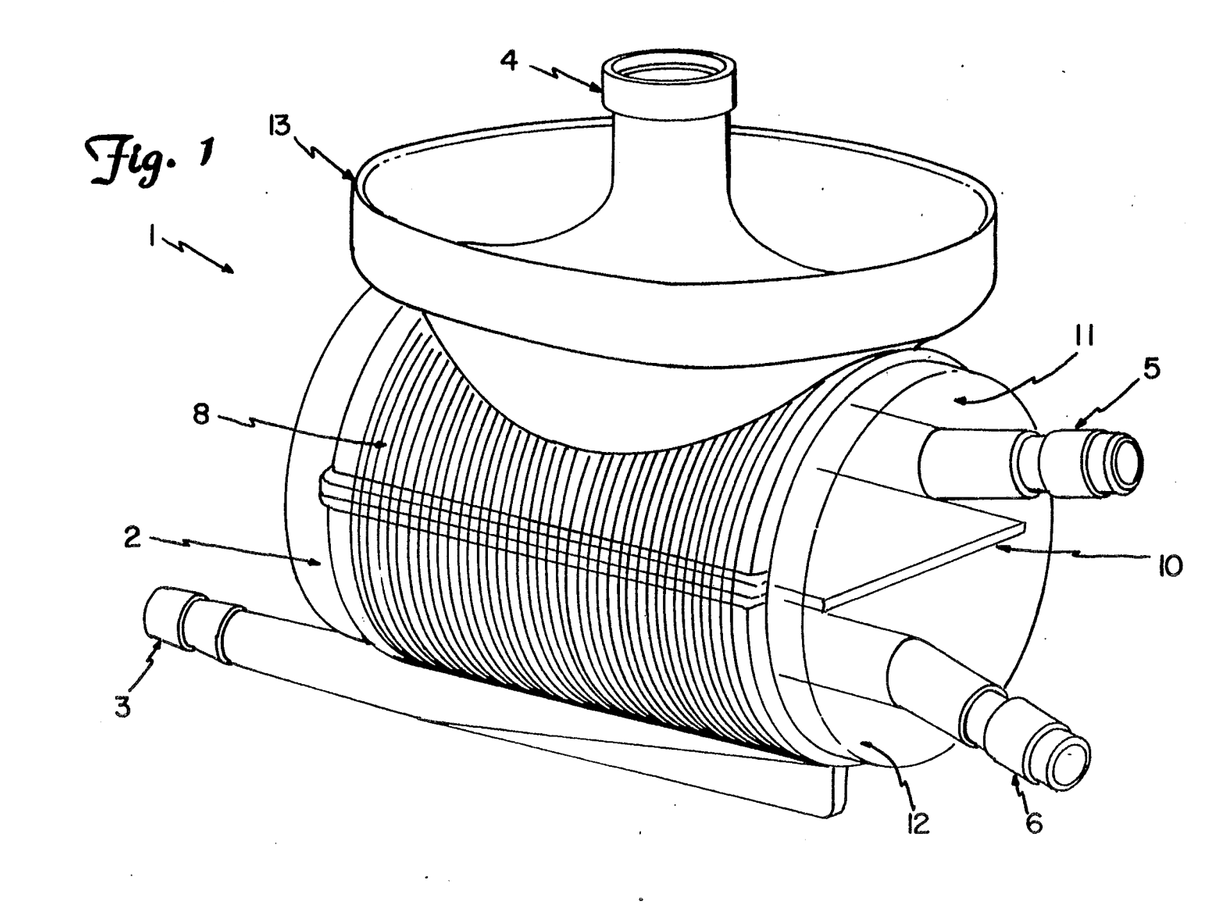
FIG. 1 is a perspective view of the present invention.
Figure 2:
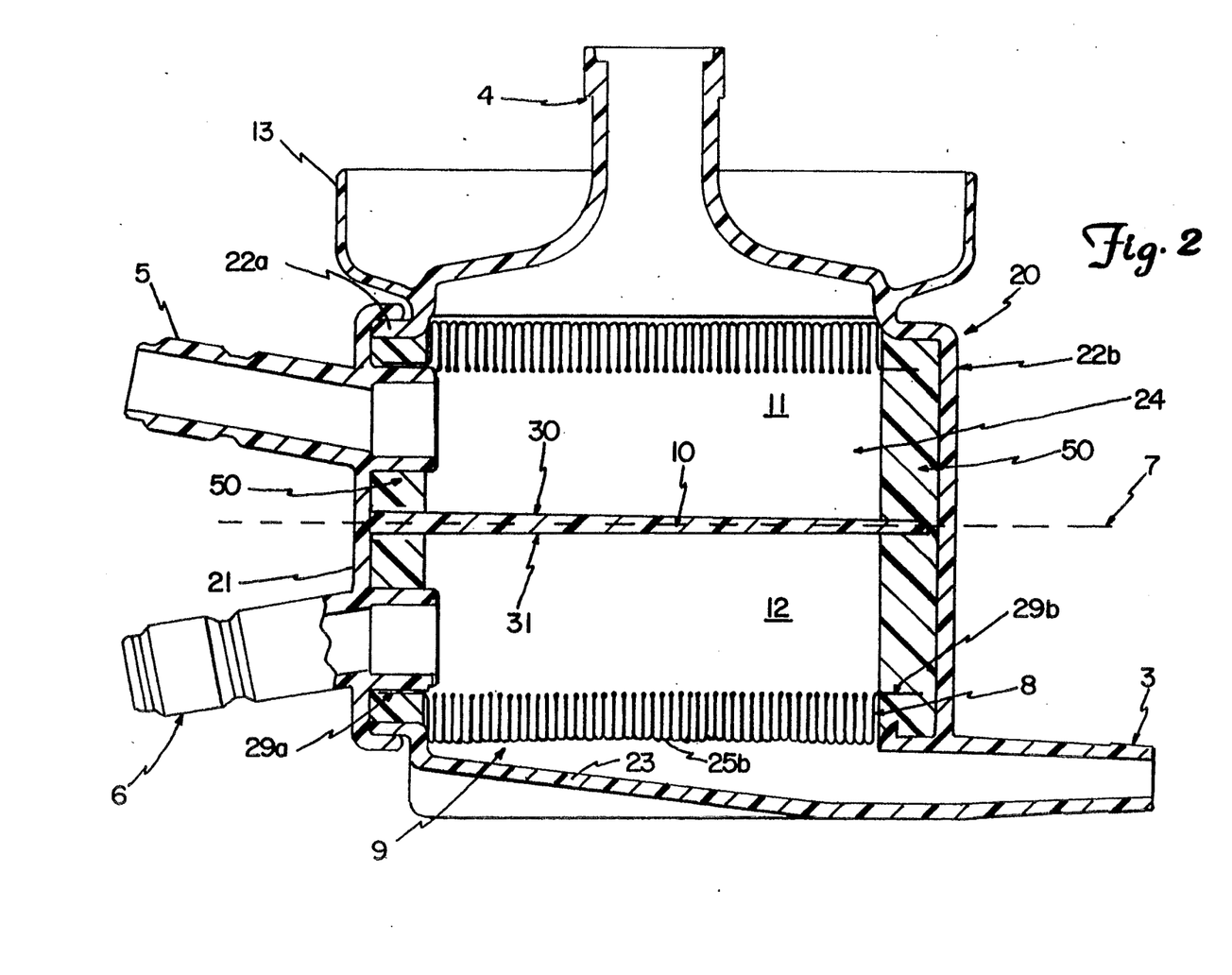
FIG. 2 is a cross-sectional view along the longitudinal axis of an embodiment of the present invention.

Referring to the drawings, the preferred embodiment of the heat exchanger of the present invention is shown therein. Referring to FIGS. 1 and 2, the heat exchanger 1 of the present invention includes a housing 2 with a first fluid inlet 3 for use as a blood inlet, a first fluid outlet 4 for use as a blood outlet, a second fluid inlet 5 for use as a heat exchange fluid inlet, and a second fluid outlet 6 for use as a heat exchange fluid outlet. Disposed coaxially along the longitudinal axis 7 of housing 2 is core 8. The outer surface of core 8 and inner surface of housing 2 define an enclosed annular blood passage chamber 9. Disposed within core 8 is a baffle 10, dividing the inner volume of core 8 into an inlet chamber 11 and an outlet chamber 12. Blood outlet 4 connects the heat exchanger to an oxygenator 13, partially shown in FIGS. 1 and 2.

As shown in FIG. 2, housing 2 is formed by an open-ended, generally cylindrical shell 20 and a cap 21. Cylindrical shell 20 has an open end 22a and a closed end 22b. Cap 21 fits over the open end 22a of shell 20 and is opposed to closed end 22b. The housing 3 has a longitudinal axis 7 that extends from cap 21 to the closed end 22b of shell 20. Cylindrical shell 20 also has continuous inner surface 23 extending between closed end 22b and cap 21 along longitudinal axis 7. An enclosed housing chamber 24 is defined by inner surface 23 of shell 20, closed end 22b, and cap 21. Shell 20 also includes blood inlet means 3 and blood outlet means 4. Shell 20 is formed by a single piece of molded plastic or other suitable material. In alternate embodiments, shell 20 is formed by two or more parts sealed together.

Core 8 is disposed coaxially along longitudinal axis 7 within housing chamber 24. Core 8 has an inner surface 25a and outer surface 25b extending along the longitudinal axis 7 between closed end 22b and cap 21. Outer surface 25b of core 8, inner surface 23 of housing 2, closed end 22b and cap 21 define an enclosed annular blood passage chamber 9. Blood inlet 3 and blood outlet 4 are in fluid communication with blood passage chamber 9. Alternatively, core 8 could be elliptical in cross section, thereby also defining an annular blood passage chamber.

In the preferred embodiment, core 8 is cylindrical, corrugated, and made of stainless steel or other material suitable for medical use. The corrugations of core 8 are created by any suitable technique. Inner surface 23, outer surface 25b of core 8, and other surfaces coming in contact with blood may be treated with heparin or other coatings commonly used on surfaces exposed to blood.

Figure 8:
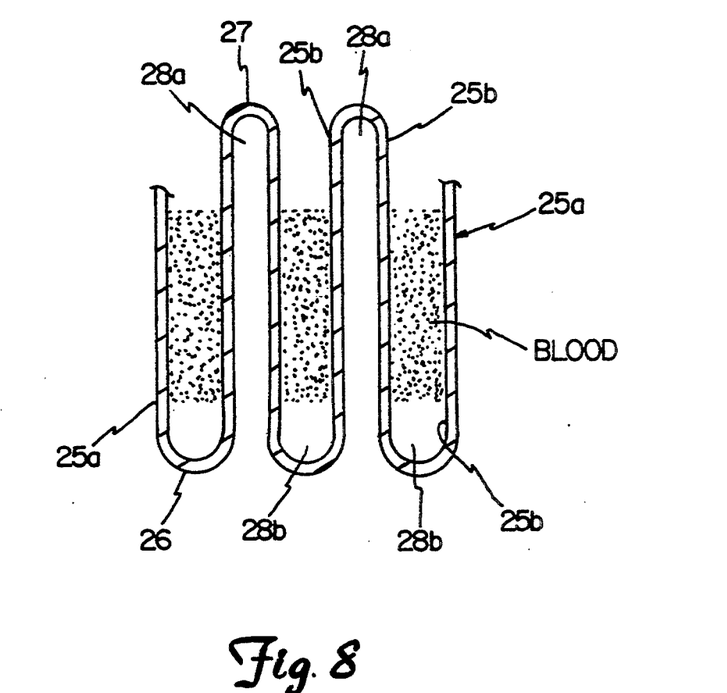
FIG. 8 is a close-up view of the corrugations of the core of an embodiment of the present invention.

In the preferred embodiment of the invention, the length of core 8 along the longitudinal axis 7 is approximately 2.7 inches and there are approximately 45 convolutions or pleats, i.e., approximately 15-18 corrugations per inch. As shown in FIG. 8, each convolute or pleat has an inner limit or root 26 which defines the inner diameter of the core, and an outer limit or crest 27 which defines the outer diameter of the core. The convolutions define inner gaps 28a on the inner surface 25a and outer gaps 28b on the outer surface 25b of the core 8. The optimal range of the distance from root to crest for each corrugation is less than one-half inch, preferably approximately 0.35 inches. As shown in FIG. 2, core 8 has proximal and distal flanges 29a, 29b extending from each end of core 8 that are used to properly seat core 8 within housing 2 as will be discussed further below.

Cap 21 fits over the open end 22a of shell 20 and includes water inlet 5 and water outlet 6. Inlet 5 and outlet 6 are tilted away from each other in order to accommodate connection of the heat exchanger to the heat exchange fluid circulation system (not shown). Heat exchange fluid inlet 5 and outlet 6 are positioned on cap 21.

Figure 3:
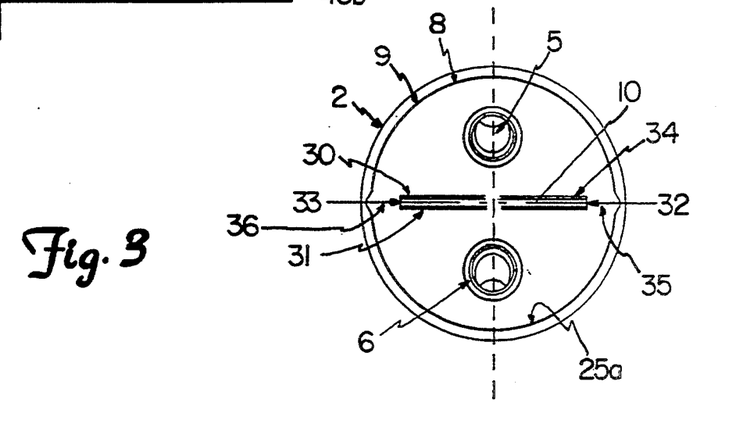
FIG. 3 is a side view of the cap end of an embodiment of the present invention.

As shown in FIG. 2, a baffle 10 is disposed within core 8 between inlet 5 and outlet 6 along the longitudinal axis. In the preferred embodiment of the invention, baffle 10 is connected to cap 21 and, as shown in FIG. 3, is oriented along the longitudinal axis 7, perpendicular to a line between the cross sectional center of inlet 5 and outlet tube 6. In an alternate embodiment of the invention, baffle 10 is oriented at an angle of approximately 45° from the line between the cross sectional center of inlet 5 and outlet 6. In the preferred embodiment of the invention, baffle 10 is planar having opposed planar faces 30, 31 and opposed lateral edges 32, 33 forming a substantially rectangular cross section 34 transverse to longitudinal axis 7. In alternate embodiments of the invention, baffle 10 can have various shapes along the longitudinal axis 7 while retaining a generally elongated cross-section transverse to the longitudinal axis 7. When cap 21 is placed over the open end 22a of shell 20, baffle 10 extends almost to the closed end 22b of shell 20. The lateral edges 32, 33 of baffle 10 are adjacent to the roots 26 of core 8.

The lateral edges 32, 33 and inner surface 25a of core 8 define elongated portals 35, 36. In the preferred embodiment of the invention where lateral edges 32, 33 extend to the roots 26, portals 35, 36 are defined by the adjacent inner gaps 28a. Alternatively, lateral edges 32 and 33 may be opposedly spaced from roots 26. Face 30, inner surface 25a, cap 21, and closed end 22b define heat exchange fluid inlet chamber 11. Inlet 5 is in fluid communication with inlet chamber 11. Face 31, inner surface 25a, cap 21, and closed end 22b define heat exchange fluid outlet chamber 12. Outlet 6 is in fluid communication with outlet chamber 12. The inlet chamber 11 and outlet chamber 12 are in fluid communication with each other through portals 35, 36. In operation, heat exchange fluid passes from fluid inlet 5 to inlet chamber 11, through portals 35, 36 into outlet chamber 12, and out fluid outlet 6.

Figure 4:
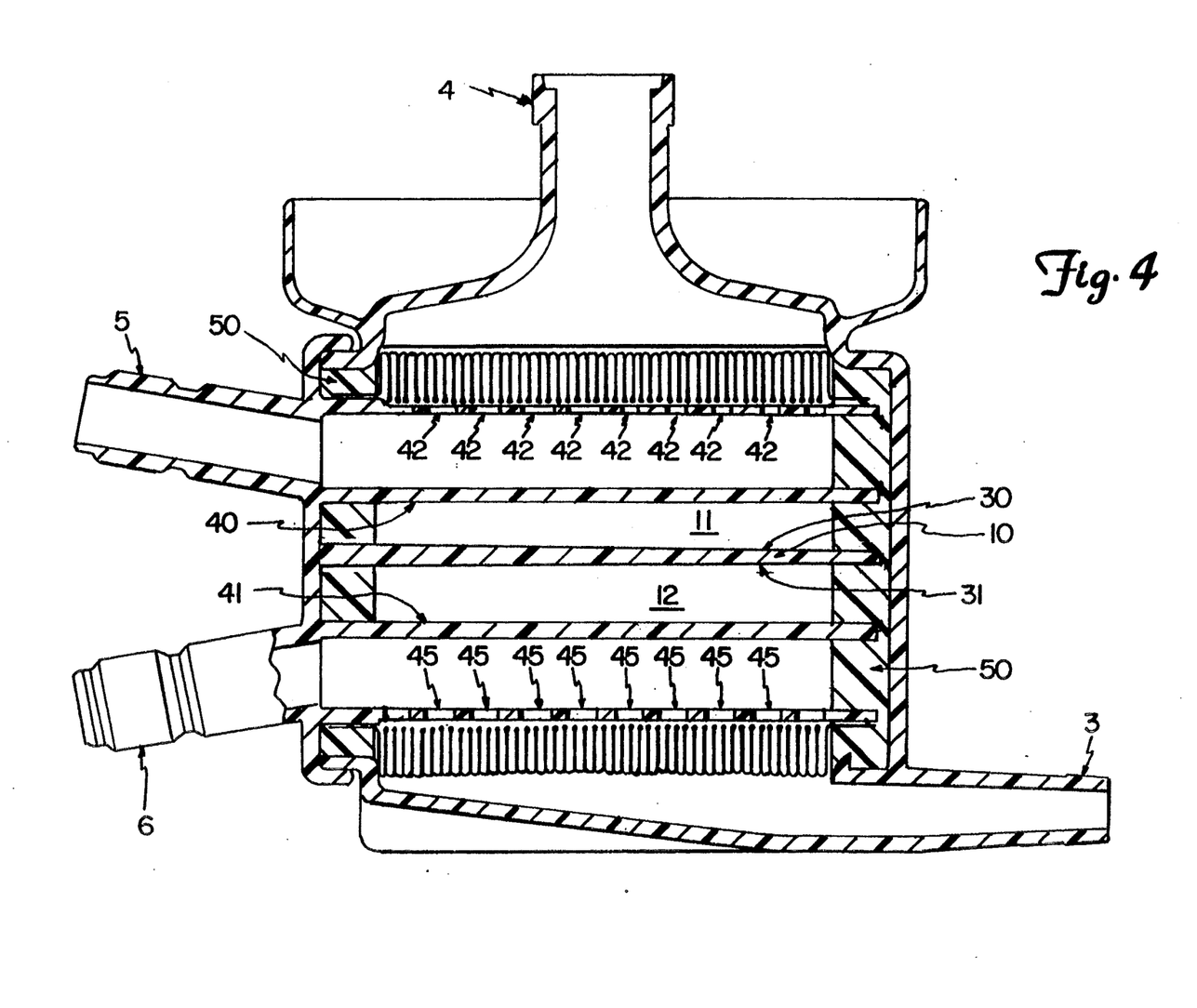
FIG. 4 is a cross-sectional view along the longitudinal axis of an embodiment of the present invention.
Figure 5:
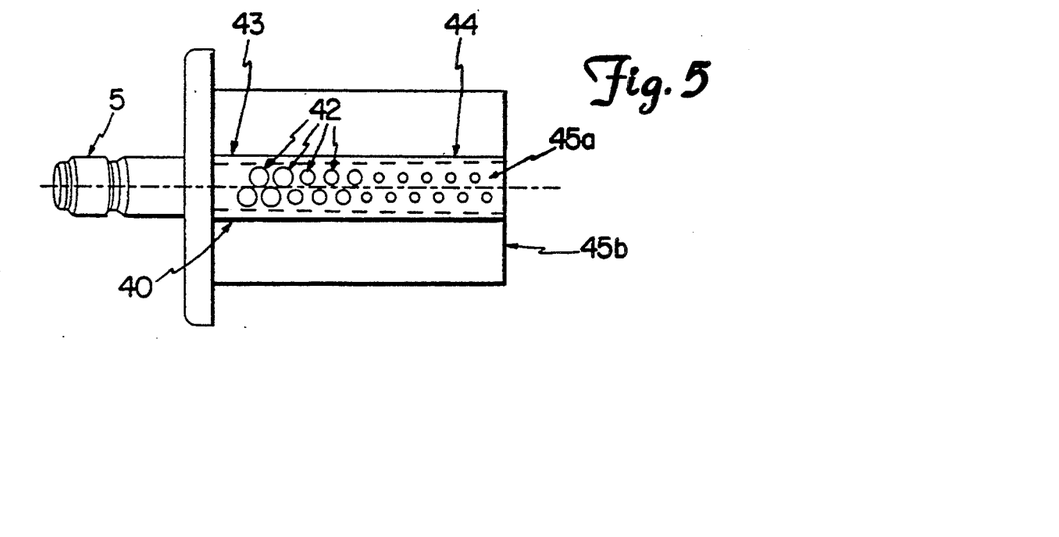
FIG. 5 is a top view of the inlet tube of an embodiment of the present invention.

In the preferred embodiment of the invention, inlet 5 and outlet 6 include heat exchange fluid inlet tube 40 and heat exchange fluid outlet tube 41, respectively, extending longitudinally into the inner volume of core 8. Inlet tube 40 extends longitudinally into inlet chamber 11, spaced from inner surface 25a and face 30. As shown in FIGS. 4 and 5, inlet tube 40 includes a plurality of apertures 42 that are adjacent to roots 26 of core 8 and directed at the inner surface 25a. The circumference of apertures 42 decrease from the proximal end 43 to the distal end 44 of inlet tube 40. This configuration produces a more uniform distribution of water flow exiting the inlet tube 40.

In the preferred embodiment of the invention, there are two offset rows 45a, 45b of apertures 42 extending substantially the longitudinal length of inlet tube 40, directing the heat exchange fluid into substantially all of the inner gaps 28a of core 8. Alternate embodiments of the invention may include apertures of different spacing and size.

Figure 6:
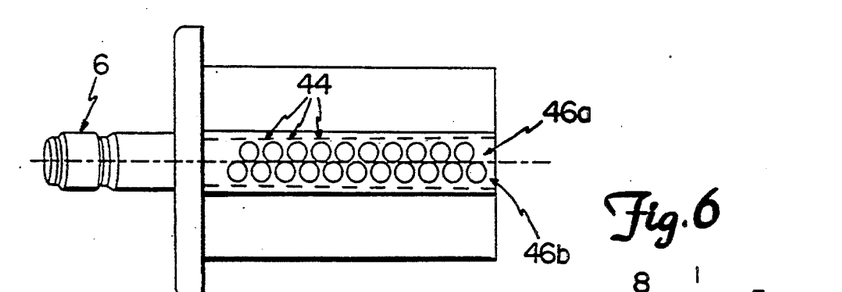
FIG. 6 is a bottom view of the outlet tube of an embodiment of the present invention.

As shown in FIGS. 4 and 6, outlet tube 41 also includes a plurality of apertures 45 spaced immediately adjacent roots 26 of corrugated core 8. In the preferred embodiment of the invention, there are two offset rows 46a, 46b of apertures 44 having the same circumference. Alternate embodiments of the invention may include various spacing of the apertures and circumference sizes. When cap 21 is placed over the open end 22a of shell 20, inlet tube 40 and outlet tube 41 extend almost to the closed end 22b of shell 20.

In a heat exchanger for use in a blood oxygenation system, it is essential that the barrier between the blood and the heat exchange fluid is liquid tight, preventing heat exchange fluid from mixing with the blood. In the present invention a potting process is used to seal the blood passage chamber 9 from the heat exchange fluid inlet and outlet chambers 11, 12; however, other sealing methods may also be used.

Potting material 50, such as polyurethane, is injected into both ends of the heat exchanger, one end at a time. As shown in FIG. 4, the potting material 50 hardens at the closed end 22b of shell 20 around the bottom ends of baffle 10, inlet tube 40, outlet tube 41, and distal flange 29b of core 8. At the cap end, the potting material 50 seals cap 21 to the open end 22a of shell 20, and also seals proximal flange 29a of core 8 in place. The potting material 50 at both ends of the heat exchanger fixes core 8 in place by surrounding the flanges 29a, 29b at each end of core 8 and extends up to at least the first corrugation at each end of core 8. Blood passage chamber 9, inlet chamber 11 and outlet chamber 12 are further defined by potting material 50 at both ends of the heat exchanger. In this embodiment, there are no dead spaces within the blood passage chamber 9 where blood might stagnate.

Figure 7:
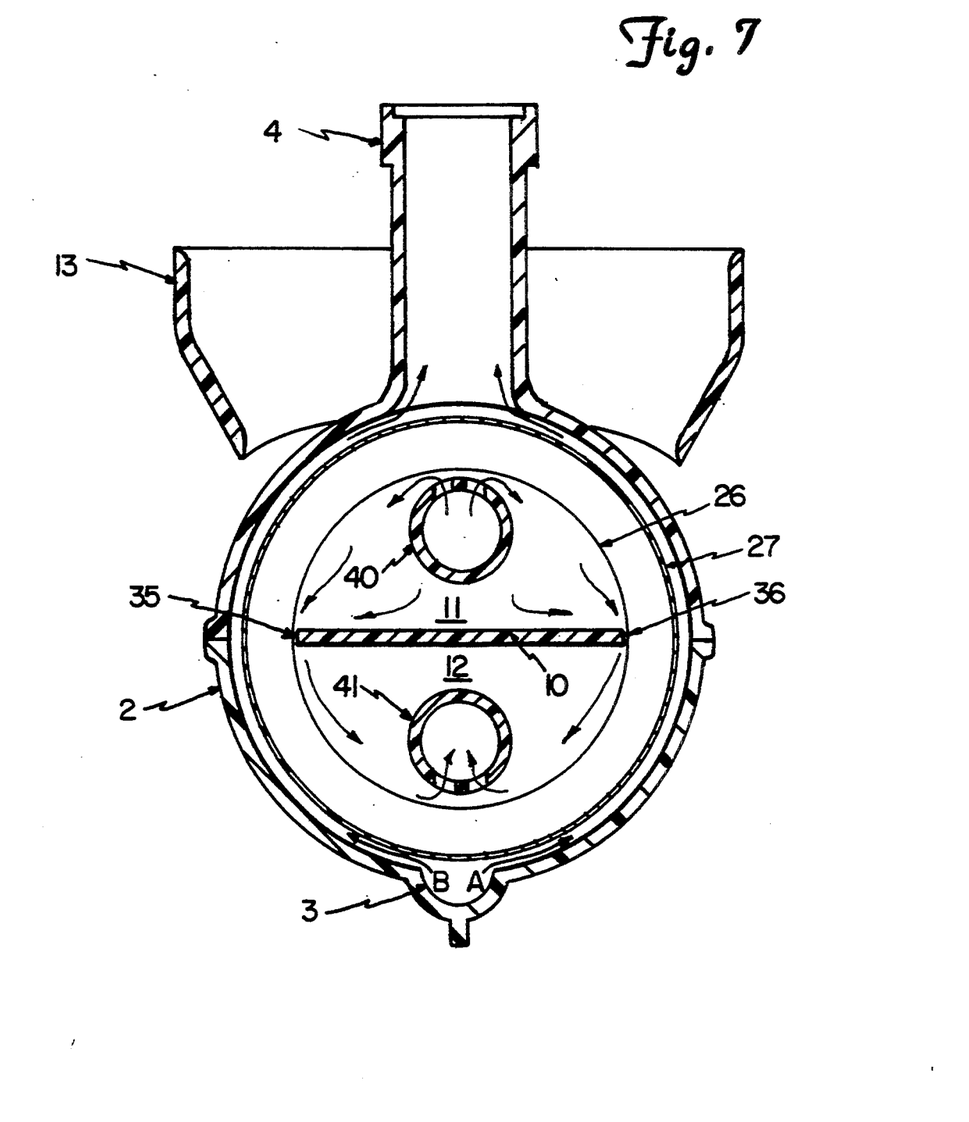
FIG. 7 is a cross-sectional view transverse to the longitudinal axis of an embodiment of the present invention.

In operation, blood flows into heat exchanger 1 through blood inlet 3 and flows into the outer gaps 28b of blood passage chamber 9. As shown in FIG. 7, blood flows in one of two circumferential routes, identified by arrows A and B, within the blood passage chamber 9 in a smooth laminar fashion. The depth of the corrugations and the distance between each corrugation is based on a trade-off between maximizing surface area for heat exchange and minimizing shear forces as blood travels through the outer gaps 28b. A typical blood flow rate is one to seven liters per minute for adults. Smaller flow rates may be used for children. Blood then exits the heat exchanger through blood outlet 4.

On the water side of the heat exchanger, water is pumped into inlet 5 at a relatively high velocity, e.g., four meters per second. A typical flow rate on the water side of the heat exchanger is ten to twenty liters per minute. The water flows through inlet 5 into inlet tube 40 where the velocity of the water is reduced and, due to the decreasing circumference of apertures 42 from the proximal end 43 to distal end 44 of inlet tube 40, the water exits through apertures 42 at roughly the same flow rates.

The water is directed into the inner gaps 28a of the inner surface 25a of core 8; however, due to the resistance of the gaps, the water tends to flow out of the gaps 28a into the open volume of the inlet chamber 11. When the water flows at a relatively high velocity from the narrow gaps 28a into the open volume, the water becomes turbulent and vortices are formed. This combination of turbulence and vortices provides a more efficient heat transfer flow pattern than a smooth laminar flow of water.

To pass around baffle 10 from inlet chamber 11 to outlet chamber 12, the water must pass through portals 35, 36. In the preferred embodiment of the invention, the portals comprise inner gaps 28a; therefore, the water must flow back into inner gaps 28a to pass around baffle 10 and into outlet chamber 12. When the water enters inner gaps 28a it becomes less turbulent and the vortices are reduced. However, once the water passes around baffle 10, it again tends to flow from the narrow inner gaps 28a into the open volume of the outlet chamber 12. Once again the water becomes turbulent and vortices are created. The water then flows into apertures 44 of outlet tube 41 and exits the heat exchanger through outlet 6.

We claim:

1. A heat exchanger for use in an extracorporeal blood circuit comprising:

(a) a housing comprising (i) opposed ends defining a longitudinal axis extending between the ends, and (ii) a continuous inner surface extending between the ends and along the longitudinal axis, forming an enclosed housing chamber;

(b) a core disposed within the housing chamber, the core comprising an inner surface and an outer surface extending between the ends along the longitudinal axis, wherein the ends, outer surface of the core and the inner surface of the housing define an enclosed annular blood passage chamber;

(c) a baffle disposed within the core and extending between the ends, the baffle having two opposed faces, two opposed edges, and an elongated cross section transverse to the longitudinal axis, wherein each edge is adjacent to the inner surface of the core, each edge and adjacent inner surface defines an elongated portal along the longitudinal axis, and one of the two opposed faces, inner surface of the core and ends defining an inlet chamber and the other of the two opposed faces, inner surface of the core and ends defining an outlet chamber, said inlet chamber and outlet chamber being in fluid communication through the portals;

(d) a blood inlet in fluid communication with the blood passage chamber;

(e) a blood outlet in fluid communication with the blood passage chamber;

(f) a fluid inlet in fluid communication with the inlet chamber and a fluid outlet in fluid communication with the outlet chamber.

2. The heat exchanger of claim 1 wherein the baffle is planar, having a substantially rectangular cross section transverse to the longitudinal axis.

3. The heat exchanger of claim 1 wherein the core is corrugated and cylindrical relative to the longitudinal axis.

4. The heat exchanger of claim 3 wherein the core has approximately 15–18 corrugations per inch measured along the longitudinal axis.

5. The heat exchanger of claim 3 wherein each corrugation has a root defining the inner limit of the corrugation and a crest defining the outer limit of the corrugation and the distance from the root to the crest of each corrugation is less than one half inch.

6. The heat exchanger of claim 1 wherein (i) the fluid inlet further comprises an inlet tube extending longitudinally from an end of the housing, said inlet tube having a plurality of apertures opening into the inlet chamber for introducing heat exchange fluid into the inlet chamber, and (ii) the fluid outlet further comprises an outlet tube extending longitudinally from an end of the housing, said outlet tube having a plurality of apertures opening into the outlet chamber for receiving heat exchange fluid from the outlet chamber.

7. The heat exchanger of claim 6 wherein the inlet and outlet tubes extend from one end to the other end of the housing.

8. The heat exchanger of claim 6 wherein the inlet and outlet tubes extend into the inlet and outlet chambers, respectively, and are spaced from the inner surface of the core and a face of the baffle.

9. The heat exchanger of claim 6 wherein the respective apertures of the inlet and outlet tubes are adjacent to the core and the apertures are directed at the inner surface of the core.

10. The heat exchanger of claim 6 wherein the respective apertures of the inlet and outlet tubes comprises at least one row of apertures extending longitudinally along the tubes.

11. The heat exchanger of claim 10 wherein the circumference of the apertures decrease in size from one end to another.

* * * * *

UNITED STATES PATENT AND TRADEMARK OFFICE
CERTIFICATE OF CORRECTION

PATENT NO. : 5,421,405
DATED : June 6, 1995
INVENTOR(S) : Goodin et al.

It is certified that error appears in the above-indentified patent and that said Letters Patent is hereby corrected as shown below:

Column 6, line 60, replace "(it)" with --(ii)--.

Column 7, line 17, after "blood passage chamber;" add --and--.

Signed and Sealed this

Eighteenth Day of November 1997

*Attest:*

BRUCE LEHMAN

*Attesting Officer*     *Commissioner of Patents and Trademarks*